United States Patent [19]

Feinstone et al.

[11] Patent Number: 5,284,760

[45] Date of Patent: Feb. 8, 1994

[54] TECHNIQUES FOR PRODUCING SITE-DIRECTED MUTAGENESIS OF CLONED DNA

[76] Inventors: Stephen M. Feinstone, 3021 Cathedral Ave., NW., Washington, D.C. 20008; Czeslaw Wychowski, 10500 Montrose Ave. #2, Bethesda, Md. 20814; Jonathan E. Silver, 7516 Arrowood Rd., Bethesda, Md. 20817; Suzanne U. Emerson, 14201 Woodcrest Dr., Rockville, Md. 20853

[21] Appl. No.: 764,085

[22] Filed: Sep. 23, 1991

Related U.S. Application Data

[63] Continuation of Ser. No. 332,616, Apr. 3, 1989, abandoned.

[51] Int. Cl.$^5$ ............................................. C12N 15/10
[52] U.S. Cl. ...................................... 435/172.3; 435/91
[58] Field of Search ............................... 435/172.3, 91

[56] References Cited

U.S. PATENT DOCUMENTS

4,683,202  7/1987  Mullis .................................. 435/91
5,023,171  6/1991  Ho ........................................ 435/6

OTHER PUBLICATIONS

Methods in Enzymology, 154:367–382, 1987, Kunkel et. al. Rapid and Efficient Site-Specific Mutagenesis without Phenotypic Selection.

Methods in Enzymology. 154:382–403, 1987, Carter Improved Oligonucleotide-Directed Mutagenesis Using M13 Vectors.

*Primary Examiner*—Robert J. Hill, Jr.
*Assistant Examiner*—John D. Ulm

[57] ABSTRACT

A method is described whereby new cDNA or RNA sequences can be introduced into or substituted for cDNA in any chosen position without specific sequence requirements using the polymerase chain reaction (PCR). The method entails the use of primers which are complementary to the 3' and 5' ends of the desired sequence to be inserted as well as to the 3' and 5' ends of the chosen site of insertion in the acceptor molecule. The desired sequence is amplified by PCR such that single stranded fragments are produced. The single stranded fragment of the desired sequence is then annealed to a single stranded acceptor molecule at the site of insertion and extended to produce a double stranded molecule. The double stranded molecule is then separated into two strands which are identical except that one of the strands contains the desired sequence inserted at the chosen site. A second double stranded molecule is then generated.

3 Claims, 11 Drawing Sheets

FIG. 1

PCR PRIMERS 1) 5' HAV/PV1 VP4 PRIMER (1ATG)

5' CATTCTTAAATAATAATGGGTGCTGAGGTTTCATC 3'

HAV 5' NON-CODING — PV1 VP4 5'END 2) 5' HAV/VP1 VP4 PRIMER (2ATG's)

5' CTTAAATAATAATGACAATGGGTGCTCAGGTTTCATC 3'

HAV 5' NON-CODING — PV1 VP4 5'END 3) 3' PV1/HAV VP4 PRIMER

3' GGGGTTACGATTTGAGCTAACTCCTTCTCGTTTAC 5'

PV1 VP4 3'END (complement) — HAV VP2 5'END (complement)

FIG. 3

FIG. 4B

Figure 4A:
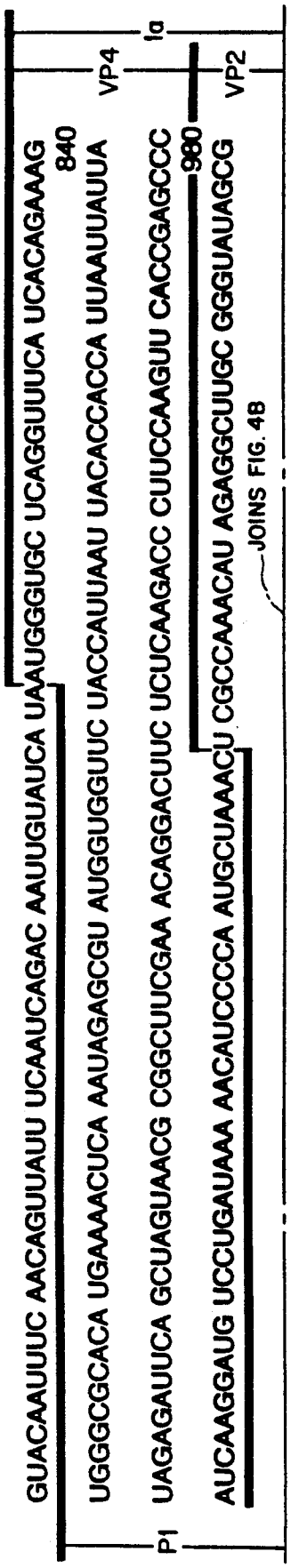

```
JOINS FIG. 4A
AUAGAGUACU GCAAUUAACA CUGGGAAACU CCACUAUAAC CACACAGGAG GCGGCUAAUU CAGUAGUCGC
                                                                          1120
UUAUGGGCGU UGGCCUGAAU AUCUGAGGGA CAGCGAAGCC AAUCCAGUGG ACCAGCGGAC AGAACCAGAC
GUCGCUGCAU GCAGGUUUUA UACGCUAGAC ACCGUGUCUU GGACGAAAGA GUCGCGAGGG UGGUGGUGGA
                                                                          1260
AGUUGCCUGA UGCACUGCGG GACAUGGGAC UCUUUGGCCA AAAUAUGUAC UACCACUACC UAGGUAGGUC
CGGGUACACC GUGCAUGUAC AGUGUAAGCG CUCCAAAUUC CACCAGGGGG CACUAGGGGU AUUCGCCGUA
                                                                          1400
CCAGAGAUGU GUCUGGCCGG GGAUAGCAAC ACCACUACCA UGCACACCAG CUAUCAAAAU GCCAAUCCUG
GCGAGAAAGG AGGCACUUUC ACGGGUACGU UCACUCCCUGA CGACAACCAG ACAUCACCUG CCCGUAGGUU
                                                                          1540
CUGCCCGGUG GAUUACCUCU UUGGAAAUGG CACGUUAUUG GGGAAUGCCU UUGUGUUCCC GCACCAGAUA
AUAAACCUAC GGACCAACAA CUGUGCUACA CUGGUACUCC CUUACGUGAA CUCCCUCUCG AUAGAUAGUA
                                                                          1680
UGGUAAAGCA CAAUAAUUGG GGAAUUUGCAA UAUUACCAUU GGCCCCAUUA AAUUUUGCUA GUGAGUCCUC
CCCAGAGAUU CCAAUCACCU UGACCAUAGC CCCUAUGUGC UGUGAGUUCA AUGGAUUAAG AAACAUUACC
                                                                          1820
CUGCCACGCU UACAGGGCCU GCCGGUCAUG AACACCCCUG GUAGCAAUCA AUAUCUUACU GCAGACAACU
UCCAGUCACC GUGUGGCGUG CCUGAAUUUG AUGUGACCCC ACCUAUUGAC AUACCCGGUG AAGUUAAGAA
                                                                          1960
CAUGAUGGAA UUGGCAGAAA UCGACACCAU GAUUCCCUUU GACUUAAGUG CACUAAAAAA GAACACCAUG
JOINS FIG. 4C
```

FIG. 4C

```
JOINS FIG. 4B

GAAAUGUAUA GGGUUCGGUU AAGUGACAAA CCACAUACAG AGGAUCCCAU ACUCUGCCUG UCACUCUCUC
                                                                      2100
CAGCUUCAGA UCCUAGGUUG UCACAUACUA UGCUUGGAGA AAUCCUAAAU UACUACACAC ACUGGGCAGG
                                                                      2240
AUCCCUGAAG UUCACGUUUC UGUUCUGUGG AUCCAUGAUG GCAACUGGCA AACUGUUGGU GUCAUACGCG
                                                                      2240
CCUCCUGGAG CCGACCCACC AAGAAGCGU AAGGAGGCGA UGUUGGGAAC ACAUGUGAUC UGGGACAUAG
                                                                      2380
GACUGCAGUC CUCAUGUACU AUGGUAGUGC CAUGGAUUAG CAACACCACG UAUCGGCAAA CCAUAGAUGA
UAGUUUCACC GAAGGCGGAU ACAUCAGCGU CUUCUACCAA ACCAGAAUAG UCGUCCCUCU UUCGACACCC

AGAGAGAUGG ACAUCCUUGG UUUUGUGUCA GCGUGUAAUG ACUUCAGGGU GCGCUUGAUG CGAGAUACCA
                                                                      2520
CACAUAUAGA GCAAAAGCG CUAGCACAGG GGUUAGGUCA GAUGCUUGAA AGCAUGAUUG ACAACACAGU

CCGUGAAACG GUGGGGGCGG CAACGUCUAG AGACGCUCUC CCAAACACUG AAGCCAGUGG ACCAGCACAC
                                                                      2660
UCCAAGGAAA UUCCGGCACU CACCGCAGUG GAAACUGGGG CCACAAAUCC ACUAGUCCCU UCUGAUACAG

UGCAAACCAG ACAUGUUGUA CAACAUAGGU CAAGGUCAGA GUCUAGCAUA GAGUCUUUCU UCGCGCGGGG
                                                                      2800
UGCAUGCGUG GCCAUUAUAA CCGUGGAUUA CUCAGCUUCC ACCAAGAAUA AGGAUAAGCU AUUUACAGUG

UGGAAGAUCA CUUAUAAAGA UACGUCCAG UUACGGAGGA AAUUGGAGUU CUUCACCUAU UCUAGAUUUG
                                                                      2940
AUAUGGAAUU UACCUUUGUG GUUACUGCAA AUUUCACUGA GACUAACAAU GGGCAUGCCU UAAAUCAAGU

JOINS FIG. 4D
```

FIG. 4D

```
                                                                    1a                                          3b
                                                                     VP1
JOINS FIG. 4C
                                                                                                3080
GUACCAAAUU AUGUACGUAC CACCAGGCGC UCCAGUGCCC GAGAAAUGGG ACGACUACAC AUGGCAAACC
                                                                                                3220
UCAUCAAAUC CAUCAAUCUU UUACACCUAC GGAACACGUC CAGCCCGGAU CUCGGUACCG UAUGUUGGUA

UUUCGAACGC CUAUUCACAC UUUUUACGACG GUUUUUCCAA AGUACCACUG AAGGACCAGU CGGCAGCACU
                                                                                                3360
AGGUGACUCC CUCUAUGGUG CAGCAUCUCU AAAUGACUUC GGUAUUUUGG CUGUUAGAGU AGUCAAUGAU

CACAACCCGA CCAAGGUCAC CUCCAAAAUC AGAGUGUAUC UAAACCCAA ACACACAGA GUCUGGUGCC
                                                                                                3500
CGCGUCCACC GAGGGCAGUG GCGUAUACGG GCCCUGGAGU GGAUUACAAG GAUGGUACGC UUACACCCCU

CUCCACCAAG GAUCUGACCA CAUAUGGAUU CGGACACCAA AACAAAGCGG UGUACACUGC AGGUUACAAA
                                                                                                3640
AUUUGCAACU ACCAUUUGGC CACUCAGGAA GAUUUGCAAA ACGCAGUGAA CGUCAUGUGG AAUAGAGACC
                                                                                        P2
UCUUAGUCAC AGAAUCAAGA GCCCAGGGCA CCGAUUCAAU CGCAAGGUGC AAUUGCAACG CAGGGUGUA

CUACUGGCGAG UCUAGAAGGA AAUACUACCC AGUAUCCCUU GUUGGCCCAA CGUCCCAGUA CAUGGAGGCU
                                                                                        JOINS FIG. 4E
  P1
```

FIG. 4E

```
JOINS FIG. 4D
AAUAACUAUU ACCCAGCUAG GUACCAGUCC CAUAUGCUCA UUGGCCAUGG AUUCGCAUCU CCAGGGGAUU
                                                                          3780
GUGGUGGGCAU ACUCAGAUGU CACCACGGGG UGAUAGGGAU CAUUACUGCU GGUGGAGAAG GGUUGGUUGC

AUUUACAGACU AUUAGAGACU UGUAUGCCUA CGAAGAAGAA GCCAUGGAAC AGGCAUCAC CAAUUACAUA
                                                                          3920
GAGUCACUUG GGGCCGCAUU UGGAAGUGGA UUUACUCAGC AGAUUGGAGA CAAAAUAACA GAGUUGACUA

AUAUGGUGAC CAGUACCAUC ACUGAAAAGC UACUAAGAA CUUGAUCAAG AUCAUAUCCU CACUAGUUAU
                                                                          4060
UAUAACUAGG AAUUAUGAAG ACACCACAAC AGUGCUCGCU ACCCUGGCCC UUCUGGGGUG UGAUGCUUCA

CCAUGGCAGU GGCUUAGAAA GAAGCAUGC GAUGUUCUGG AGAUACCUUA UGUCACCAAG CAAGGUGACA
                                                                          4200
GUUGGUUGAA GAAGUUUACU GAAGCAUGCA ACGCAGCUAA GGGACUGGAG UGGGUGUCAA ACAAAAUCUC

AAAAUUCAUU GAUUGGCUCA AGGAGAAAU UAUCCCACAA GCUAGAGAUA AGUUGGAAUU UGUAACAAA
                                                                          4340
CUUAGACAAC UAGAAAUGCU GGAAAACCAA AUCUCAACUA UACACCAAUC AUGCCCUAGU CAGGAACACC

AGGAAAUUCU AUUCAAUAAU GUCAGAUGGU UAUCCAUCCA GUCUAAGAGG UUUGCCCCUC UUUACGGAGU
                                                                          4480
GGAAGCCAAA AGAAUACAGA AACUAGAGCA UACCAUUAAC AACUACAUAC AGUUCAAGAG CAAACACCGU

AUUGAACCAG UAUGUUUGCU AGUAGCAUGG AGCCCCGGAA CAGGUAAAUC UGUAGCAACC AACCUGAUUG
                                                                          4620
CUAGAGCCAU AGCUGAGGG GAAAACACGU CCACGUACUC GCUACCCCCG GAUCCAUCAC ACUUCGACGG

JOINS FIG. 4F
```

FIG. 4F

```
                                                JOINS FIG. 4E
     AUACAAACAA CAGGGAGUGG UGAUUAUGGA CGACCUGAAU CAAAACCCAG AUGGUGCGGA CAUGAAGCUG
                                                                              4760
     UUCUGUCAGA UGGUAUCAAC AGUGGAGUUU AUACCACCCA UGGCAUCCCU GGAGGAGAAA GGAAUCCUGU
     UUACUUCAAA UUACGUUCUA GCAUCCACGA ACUCAAGCAG AAUUCCCCC CCCACUGUGG CACACAGUGA
                                                                              4900
  P2 UGCAUUAGCC AGGCGCUUUG CGUUCGACAU GGACAUUCAG GUCAUGAAUG AGUAUUCUAG AGAUGGGAAA
     UUGAACAUGG CCAUGGCUAC UGAAAUGUGU AAGAACUGUC ACCAACCAGC AACUUUAAG AGAUGCUGUC
                                                                              5040
     CUUUAGUGUG UGGUAAGGCA AUUCAAUUAA UGGACAAAUC UUCCAGAGUU AGAUACAGUA UUGACCAGAU
     CACUACAAUG AUUAUCAAUG AGAGAAACAG AAGAUCCAAC AUUGGCAAUU GUAUGGAGGC UUUGUUCCAA
                                                                              5180
     GGACCACUCC AGUAUAAAGA CUUGAAGAUU GACAUCAAGA CGAGUCCCCC UCCUGAAUGU AUCAAUGACU
     UGCUCCAAGC AGUUGACUCC CAGGAGGUGA GAGAUUACUG UGAGAAGAAG GGUUGGAUGU UCAACAUCAC
                                                                              5320
     CAGCCAGGUU CAAACAGAAA GGAACAUCAA CAGGGCAAUG ACAAUUCUAC AGCGGUGAC AACCUUCGCC
                                                                    VPg
     GCAGUGGCUG GAGUUGUCUA UGUCAUGUAU GGUUCAUGAC CUGGACACCA GGGAGCAUAC ACUGGUUUAC
                                                                              5460
  P3 CAAACAAAAA ACCCAACGUG CCCACCAUUA GGACAGCAAA GGG CCAGGUUCG AUUACGCAGU
     GGCUAUGGCU AAAAGAAACA UUGUUACAGC AACUACUGGC AGGGAGAGU UCACUAUGUU AGGAGUCCAA
                                                                              5600
     GACAACGUGG CUAUUUUACC AACCCACGCU UCACCUGGUG AAAGCAUUGU GAUCGAUGGC AAAGAGUGG
                                                JOINS FIG. 4G
```

FIG. 4G

JOINS FIG. 4F

AGAUCUUGGA UGCCAAAGCG CUCGAAGAUC AAGCAGGAAC CAAUCUUGAA AUCACUAUAA UCACUCUAAA
                                                                                                        5740

GAGAAAUGAA AAGUUCAGAG ACAUUAGACC ACAUAUACCU ACUCAAAUCA CUGAGACAAA UGAUGGAGUC

UUGAUCGUGA ACACUAGCAA GUACCCCAAU AUGUAGUGUUC CUGUCGGUGC UGUGACUGA CAGGGAUAUC
                                                                                                        5880

UAAAUCUCGG UGGGGCCAA ACUGCUCGUA CUCUAAUGUA CAACUUUCCA ACCAGAGCAG GACAGUGUGG

UGGAGUCAUC ACAUGUACUG GGAAAGUCAU CGGGAUGCAU GUUGGUGGGA ACGGUUCACA CGGGUUUGCA
                                                                                                        6020

GCGGCCCUGA AGCGAUCAUA CUUCACUCAG AGUCAAGGUG AAAUCCAGUG GAUGAGACCU UCGAAGGAAG

UGGGAUAUCC AAUCAUAAAU GCCCCGUCCA AAACCAAGCU UGAACCCAGU GCUUUCCACU AUGUGUUUGA
                                                                                                        6160

AGGGGUGAAG GAACCAGCAG UCCUCACUAA AACGAUCCC AGGCUUAAGA CAAACUUUGA GGAGGCAAUU

UUCUCCAAGU ACGUGGGUAA CAAAUUACU GAAGUGGAUG AGCACAUGAA AGAGGCAGUA GACCACUAUG
                                                                                                        6300

CUGGCCAGCU CAUGUCACUA GACAUCAACA CAGAACAAAU GUCCACCAG UGCUGGGAG GAUGCCAUGU AUGGCACUGA

UGGUCUAGAA GCACUUGAUU UGUCCACCAG UGCUGGGAA CCUUAUGUAG CAAUGGGAAA GAAGAAGAGA
                                                                                                        6440

GAUAUCUUGA ACAAACAAAC CAGAGACACU AAGGAUGAAC UUAGAUCCAA ACAAAGGUU GAGCAGGGGA AAUCCAGAUU

UCCCACUGGU GAGUUAUGUA AAGGAAGGAAC CAGAGACACU AACAAGGUU GAGCAGGGGA AAUCCAGAUU
                                                                                                        6580

AAUUGAAGCU UCUAGAUUUGA AUGACUCAGU GGCAAUGAGA AUGGCUUUUG GAACCUAUA UGCUGCUUUU

JOINS FIG. 4H

FIG. 4H

JOINS FIG. 4G

CACAAAAACC CAGGAGUGAU AACAGGUUCA GCAGUAGGGU GCGAUCCAGA UUUGUUUUGG AGCAAAAUUC 6720
CGGUAUUGAU GGAAGAGAAG CUGUUUGCCU UUGACUACAC AGGGUAUGAU GCAUCUCUCA GCCCUGCUUG 6790
GUUCGAGGCA CUAGAGAUGG UGCUUGAGAA AAUCGGAUUC GGAGACAGAG UUGACUACAU CGACUACCUA 6860
AACCACUCAC ACCACCUGUA CAAGAAUAAA ACAUACUGUG UCAAGGGCGG UAUGCCAUCU GGUUGCUCAG 6930
GCACUUCAAU UUUUAACUCA AUGAUUAACA ACUUGAUUAU CAGGACACUC UUACUGAAAA CCUACAAGGG 7000
CAUAGAUUUA GACCACCUAA AAAUGAUUGC CUAUGGUGAU GAUGUAAUUG CUUCCUACCC CCAUGAAGUU 7070
GACGCUAGUC UCCUAGCCCA AUCAGGAAAA GACUAUGGAC UAACUAUGAC UCCAGCUGAC AAAUCAGCUA 7140
UAUUUGAAAC AGUCACAUGG GAGAAUGUAA CAUUCUUGAA GGAAUUCAU GAAUCAAUA GAUCCUAGG 7210
AUUUCUUAUU CAUCCAGUAA UGCCAAUGAA UGCACAAUGG CGAAGAAGAA UAUAACAAAU AGAUCCUAGG 7280
AACACUCAGG AUCAGUUCG CUCUCUGUGC CUAUUAGCUU GGCACAAUGG CGAAGAGCUUU AUUGCUCCCA GAGUACUCAA UAUGAUGG 7350
UCCUAGCUAA AAUCAGGAGU GUGCCAAUUG GAAGAGCUUU AUUGGAUUGG GUCAUACUGC UGUAGGGGUA 7420
CCGUUGGCUU GACUCAUUUU AGUAACCCUA CCUCAGUCGA AUUGGAUUGG GUCAUACUGC UGUAGGGGUA 7420

P3 7440

AAUUUUUCUU UAAUUCGGAG G-poly(A)

TECHNIQUES FOR PRODUCING SITE-DIRECTED MUTAGENESIS OF CLONED DNA

This is a continuation of application Ser. No. 07/332,616, filed on Apr. 30, 1989, which was abandoned upon the filing hereof Sept. 23, 1991.

This invention provides a new method of producing site-directed mutagenesis of cloned DNA using the polymerase chain reaction (PCR).

BACKGROUND OF THE INVENTION

Infectious cDNA clones of picornaviruses have been produced in several laboratories following the poliovirus (PV) work of Racaniello (*Science* 214, 916-919). Chimeric PV's have been made in which short portions of one type of complementary cDNA from one type of picornavirus DNA has been inserted into the infectious cDNA of another type of PV (Martin, et al., *EMBO Journal*, 7, (1988) 2839-2847). Long segments have also been exchanged between PV types (Korhara, et al., *J. Virol*, 62 (1988), 2828-2835). Chimeras of PV and hepatitis A virus (HAV) have also been produced in several laboratories in which small segments of HAV cDNA representing putative antigen coding regions have been inserted into infectious cDNA of PV. However, none of these constructs have produced viruses that express HAV antigens. It is possible that the correct coding regions have not been inserted, but it is also likely that the epitopes of HAV are conformational. For instance, we have produced an "epitope library" in lambda gtll consisting of random fragments of the HAV capsid coding region. When this library was screened with neutralizing monoclonal antibodies to HAV, no clones were detected. However, when the library was screened with antibodies to synthetic oligopeptides representing regions VP1, VP2, VP3, and VP4, many positive clones were identified. These results suggest that the neutralization epitopes of HAV are non-linear. It is possible that a complete copy of one of the capsid proteins expressed as part of the PV capsid would assume the necessary three dimensional structure to represent a neutralizing epitope of HAV. In the past chimeric cDNA's with large inserts have been difficult to make requiring either the presence of convenient restriction enzyme sites or sophisticated and complicated genetic engineering. In fact, common restriction sites rarely exist in different viral species such as HAV and PV.

SUMMARY OF THE INVENTION

The new method of the invention that has been developed enables the construction of chimeric viruses with relatively large inserts and without regard to the restriction enzyme sites or other considerations of viral genomic sequence. The invention provides a method by which new cDNA fragments may be introduced into or substituted for cDNA in any chosen position within cloned DNA without regard to the position of specific restriction enzyme sites or any other specific sequence requirements. The method requires preparation of a construct by polyymerase chain reaction (PCR) comprising a selected strand of donor DNA or RNA by annealing a primer pair at each end.

The method requires preparation of DNA segment by the polymerase chain reaction in which oligonucleotide polymerase primers are designated such that the 3′ portion of the primer anneals by nucleotide base complementarity to the precise 3′ end of the desired source DNA or RNA and the 5′ portion of the primer anneals by nucleotide complementarity to the precise location in the acceptor DNA where the 3′ end of the source DNA is to be inserted. In a similar way, the primer for the 5′ end of the source DNA is designated in which the 3′ end of the primer anneals to the precise position that defines the complement of the 5′ end of the DNA to be inserted and the 5′ end of the primer anneals to the precise location in the acceptor DNA where the 5′ end of the donor DNA is to be inserted.

While the method of the invention can be used to insert smaller fragments, the method is particularly useful when larger segments are inserted. This method can be efficiently used to replace or insert segments of nucleic acid of from about 60 to 2000 bases or more. Since, in the past, such manipulations were either limited in size, required convenient restrictions enzyme sites, or complicated genetic engineering, the development of a rapid, simple method in which essentially any segments of DNA or RNA can be placed into a clone precisely where desired without restriction enzyme sites or complicated manipulations provides a real advantage over the prior art.

DESCRIPTION OF THE FIGURES

FIG. 1 PCR primers are exemplified which are useful for use in the method of the invention.

FIG. 2 An figurative depiction of the process as disclosed in example 1 using primers depicted in FIG. 1.

Figure 3:
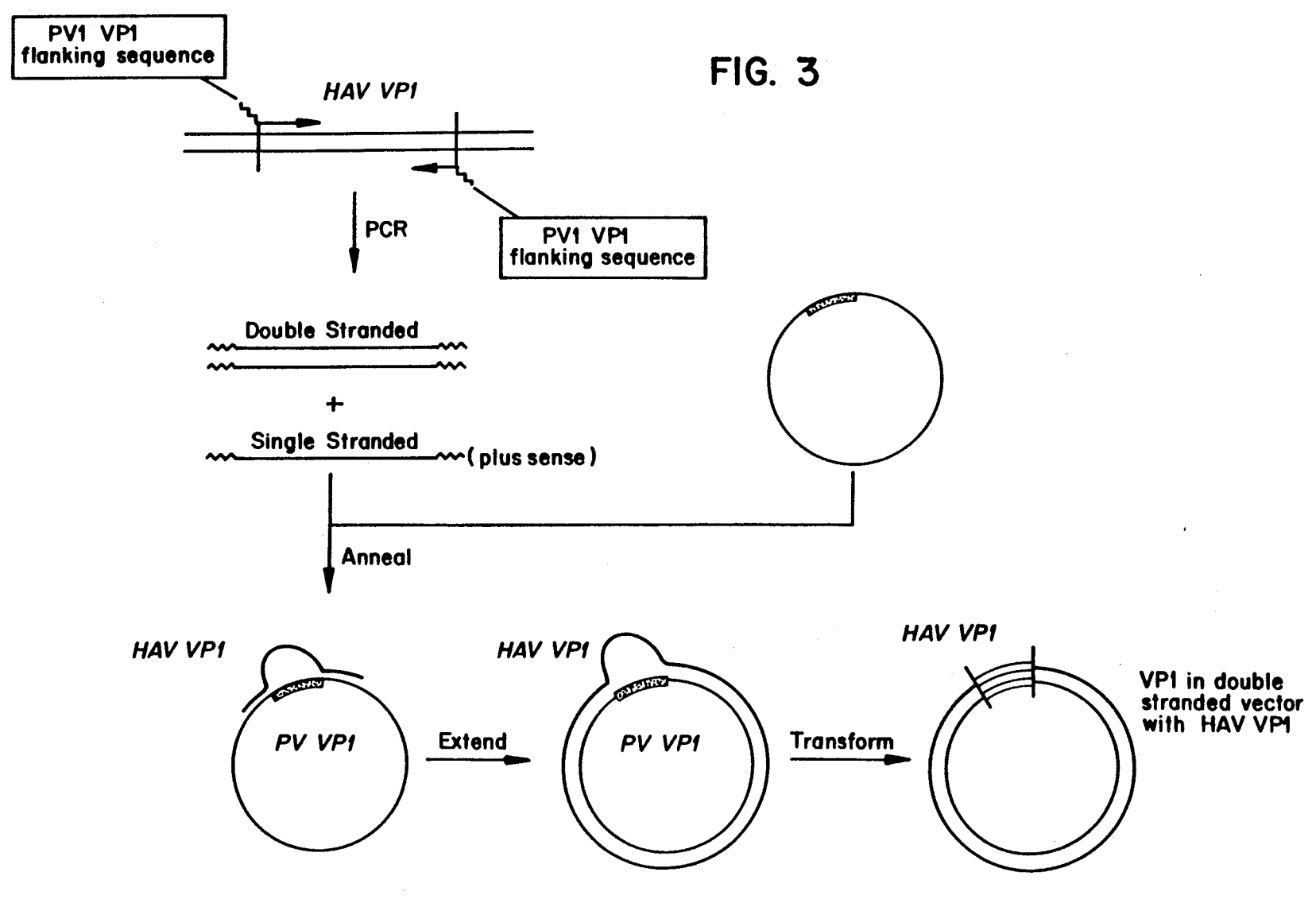

FIG. 3 A figurative depiction of the process as disclosed in example 2.

FIGS. 4A to H The full length poliovirus used in the construct is shown. The VP4 region was inserted into the HAV VP4 site.

DETAILED DESCRIPTION OF THE INVENTION

The invention provides means of replacing a segment of the accepting DNA strand with a precisely chosen sequence of interest from a DNA or RNA template by polymerase chain reaction (PCR) using PCR oligonucleotide primers chosen for the precise sequence. These primers have an additional sequence at their 5′ ends that will specifically hybridize with regions of the target cloned DNA exactly where the amplified DNA is to be inserted. The fragment is then inserted by techniques similar to oligonucleotide site directed mutagenesis except that the PCR fragment is used instead of a mutagenic oligonucleotide. By using a limiting amount of one PCR primer, single strands can be produced in the PCR reaction. These single strands are equivalent to a mutagenic oligonuclotide, but they may be much longer, allowing for insertion or substitution of large DNA fragments into the acceptor DNA.

A modification of the polymerase chain reaction (PCR) using known means (See, for example, Saiki, et al., *Science,* 230 (1985), 1350–1354) was used to produce a single stranded DNA from either cloned cDNA or directly from Viral RNA (See Gyllensten, et al., *Proc. Nat. Acad. Sci, USA,* 85 (1988) 7652–7656).

The primers are designated to amplify precisely the region that is intended to be transferred. The 5′ end of the primers is extended to include a sequence complementary to the precise position of the target cDNA where the insertion is to be made. The target cDNA is cloned into a "phagemid" and single stranded circular DNA is produced by coinfection with M 13 helper phage. Single strands are produced in the PCR reaction by reducing the concentration of the appropriate primer to approximately 1/100th the normal luM concentration used in the PCR reaction. The single stranded PCR product is used like a mutagenic oligonucleotide in a site directed mutagenesis scheme as described by Zollar and Smith (*Nucl. Acids Res.* 10, (1982) 6487-6500) or one of the variations of that techniques (See Taylor, et al., *Nucl. Acids Res.* 13 (1985) 8764-8785.).

EXAMPLE 1

Figure 2:
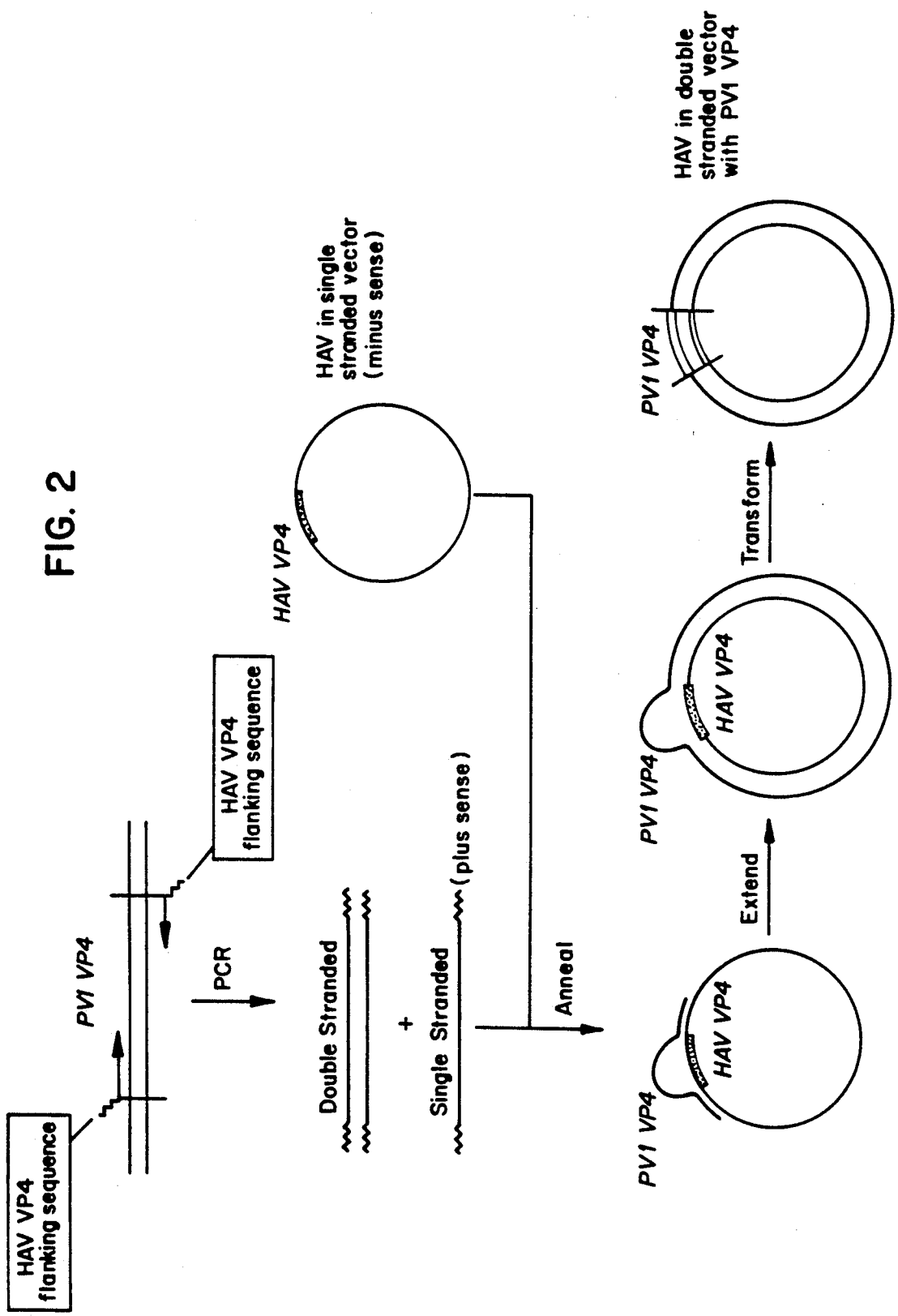

Synthesis of Chimeric Hepatitis a Virus/Poliovirus Subgenomic cDNA by a PCR Mutagenesis System Using a modification of the Eckstein mutagenesis techniques (Taylor, et al, *Nucleic Acids Res*, 1985) and PCR, a subgenomic cDNA chimera of hepatitis A virus (HAV) in which the precise HAV VP4 coding region was replaced by the VP4 coding region of Sabin type 1 poliovirus (PV1) was created. The method involved use of the PCR primers for the PV1 VP4 gene that had HAV VP4 flanking sequences on their 5'ends (see FIGS. 1 and 2). Single stranded DNA was produced by using a limiting amount of one of the primers in the PCR reaction (Gyllenstein and Erlich, *PNAS*, 1988). This single stranded DNA was used like a mutagenic oligonucleotide on a single stranded phagemid containing the first 2070 bases of the HAV genome and mutagenesis was carried out by the Eckstein method. Clones were isolated that had the PV1 VP4 substituted for the HAV VP4 as determined by DNA sequencing. This method was rapid, efficient, and overcame most of the difficulties of earlier methods.

EXAMPLE 2

Synthesis of Chimeric Poliovirus/Hepatitis a Virus Wherein the VP1 Coding Region of the Hepatitis is Inserted Into Poliovirus VP1 Site.

The coding region of the hepatitis A virus was inserted into a poliovirus at the VP1 site. The polio VP1 was completely replaced by hepatitis A virus VP1 coding region. The new construct was transfected into tissue culture/Poliovirus/HAV chimera expressing some hepatitis A antigens and some polio antigens can be obtained thereby.

Discussion

Constructs of the present invention may be used to provide several useful products, including vaccines, growth factors, and antigens for use as diagnositic agents. One of ordinary skill in the art will readily ascertain the many uses for which constructs can be provided by the method of the invention.

Antigens produced from clones made by the method of the invention can be used to provide antibodies by known means. Antigens and antibodies may be used in antigen-antibody assays, such as the ELISA test to detect antibodies which bind to antigens produced by means of the invention.

We claim:

1. A method of incorporating a DNA or RNA sequence of at least 60 bases into an acceptor DNA at a specific site comprising the steps of:
   i) producing a first primer wherein the 3' end of said first primer is capable of annealing to the 3' end of a DNA or RNA having said DNA or RNA sequence and the 5' end of said first primer is capable of annealing to a first end of the insertion site of said acceptor DNA;
   ii) producing a second primer wherein the 3' end of said second primer is capable of annealing to the complement of the 5' end of said DNA or RNA and the 5' end of said second primer is capable of annealing to a second end of the insertion site of said acceptor DNA;
   iii) amplifying said DNA or RNA sequence using said first primer and said second primer under conditions such that a single stranded molecule is produced wherein said molecule has a 3' end which anneals to the first end of the insertion site of said acceptor DNA and 5' end which anneals to the second end of the insertion site of said acceptor DNA;
   iv) contacting said single stranded molecule with said acceptor DNA under conditions such that annealing occurs;
   v) extending said annealed single stranded molecule such that a first double stranded heteroduplex molecule is obtained;
   vi) separating the strands of said first double stranded molecule; and
   vii) generating a second double stranded molecule wherein each strand contains said DNA or RNA sequence or complement thereof.

2. The method according to claim 1 wherein said DNA or RNA sequence is between 60 and 2000 bases.

3. The method according to claim 1 wherein said acceptor DNA is a phagemid.

* * * * *